United States Patent [19]

Fletcher et al.

[11] 4,064,566
[45] Dec. 27, 1977

[54] METHOD OF ADHERING BONE TO A RIGID SUBSTRATE USING A GRAPHITE FIBER REINFORCED BONE CEMENT

[76] Inventors: James C. Fletcher, Administrator of the National Aeronautics and Space Administration, with respect to an invention of; Albert C. Knoell, La Crescenta; Hugh G. Maxwell, La Canada, both of Calif.

[21] Appl. No.: 674,194

[22] Filed: Apr. 6, 1976

[51] Int. Cl.² ............................................... A61F 1/24
[52] U.S. Cl. .................................... 3/1.9; 128/92 C; 128/92 G; 260/42.17
[58] Field of Search .............................. 3/1.9–1.913; 128/92 C, 92 CA, 92 R, 92 G; 260/42.17; 32/15, 10 A

[56] References Cited

U.S. PATENT DOCUMENTS 3,848,273  11/1974  Frey ..................................... 3/1.913

OTHER PUBLICATIONS

"Medical & Dental Applications of Cements" by D. C. Smith, Journal of Biomedical Materials Research Symposium, vol. 1, 1971, pp. 189–205.

"The Selection of Implant Materials", Chapter 6, by D. F. Williams, Implants in Surgery, (book), by Williams & Roaf, W. B. Saunders Co. Ltd., (publisher) July 1973, pp. 323–326.

"Quartz and Graphite Filament Reinforced Polymer Composites for Orthopedic Surgical Application" by S. Musikant, Journal of Biomedical Materials Research Symposium, vol. 1, 1971, pp. 225–235.

*Primary Examiner*—Ronald L. Frinks
*Attorney, Agent, or Firm*—Monte F. Mott; Wilfred Grifka; John R. Manning

[57] ABSTRACT

A method of adhering bone to the surface of a rigid substrate such as a metal or resin prosthesis using an improved surgical bone cement. The bone cement has mechanical properties more nearly matched to those of animal bone and thermal curing characteristics which result in less traumatization of body tissues and comprises a dispersion of short high modulus graphite fibers within a bonder composition including polymer dissolved in reactive monomer such as polymethylmethacrylate dissolved in methylmethacrylate monomer.

7 Claims, 1 Drawing Figure

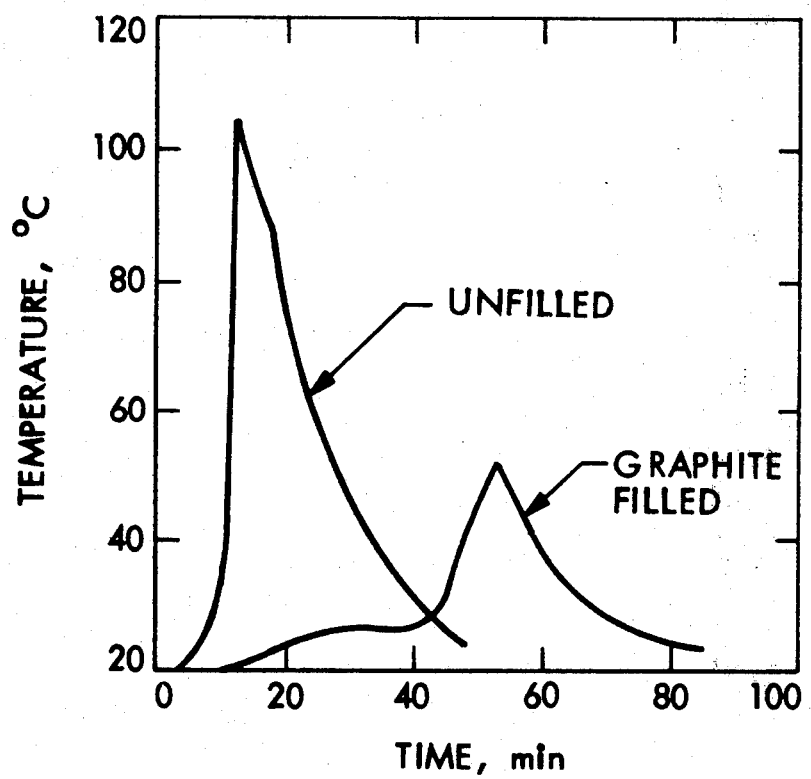

METHOD OF ADHERING BONE TO A RIGID SUBSTRATE USING A GRAPHITE FIBER REINFORCED BONE CEMENT

ORIGIN OF THE INVENTION

The invention described herein was made in the performance of work under a NASA contract and is subjected to the provisions of Section 305 of the National Aeronautics and Space Act of 1958, Public Law 83-568 (72 Stat. 435; 42 USC 2457).

BACKGROUND OF THE INVENTION

1. Field of the Invention

The present invention relates to improved surgical bone cement compositions and, more particularly, to a graphite fiber reinforced bone cement of the acrylic type.

2. Description of the Prior Art

The bio-compatible surgical bone cements previously available for use in orthopedic surgery have several drawbacks. The strength of these materials is marginal and curing produces a relatively high exothermic temperature which has a traumatizing effect on body tissues. Fiber reinforced resin composites have previously been used as components of skeletal prosthetics. However, such materials are not suitable as bone cements for directly adhering bone to bone or for adhering metal or resin surfaces of the prosthesis to the existing bone.

The bone cement is present at the interface between fairly stiff bone material and the opposing bone surface or the fairly rigid exterior of the prosthesis. The presently available bone cements cure to form a fairly soft, pliable material which does not maintain the prosthesis firmly in place and is subject to separation at either interface due to mechanical stress.

SUMMARY OF THE INVENTION

An improved surgical bone cement is provided in accordance with the invention which has mechanical properties more nearly matched to those of bone and thermal curing characteristics which result in less traumatization of body tissues during curing. The surgical bone cement of this invention has improved strength and stiffness, a reduced thermal expansion coefficient and sustains a lower exothermic temperature reaction during curing which is found to be about half of that experienced with the prior materials.

The bone cement of the invention cures to a high strength stiff material providing a stiff interface more nearly matched to that of bone and offers the potential for good adherence to the bone and prosthesis thus providing for improved performance of the total implant system.

The bone cement composition of the invention comprises a dispersion of from 2 to 12% by weight of short fine high modulus graphite fibers within a solution of biocompatible polymer dissolved in reactive monomer. The polymer content of the composition is preferably from 50 to 70% by weight and the monomer from 20 to 40% by weight. The composition may also contain cross-linking agents, free radical catalysts and activators therefor and other additives such as plasticizers, chain transfer agents and inhibitors.

The composition is prepared by first forming a slurry of the solid polymer in the liquid monomer and then adding the graphite fibers and the curing agents to the mixture and intimately dispersing them therein. The pot life or cure time of the composition will depend on curing agents and polymeric and monomeric ingredients. The viscous, pasty cement is then applied to the bone and/or prosthesis interfaces during surgical use and allowed to cure. After cure, a firm, adherant interfacial bond will be formed with the bone and prosthesis and the cement will be a stiff flexural material capable of withstanding stresses encountered in the skeletal system. The addition of fiber to the monomer polymer system serves to preserve material isotropy during clinical applications.

These and many other attendant advantages of the invention will become apparent as the invention becomes better understood by reference to the following detailed description when considered in conjunction with the accompanying drawing.

BRIEF DESCRIPTION OF THE DRAWING

The FIGURE is a set of graphical exothermic cure data for unfilled bone cements and graphite filled bone cements in accordance with the invention.

DESCRIPTION OF THE PREFERRED EMBODIMENTS

The graphite fibers utilized in the invention are high modulus materials prepared by converting an organic precursor into a high strength, high modulus fiber. The precursor is converted by a first stage conversion to a carbon fiber during which the material is heated usually in the presence of oxygen and usually under tension. Under applications of heat typically up to a temperature of about 450° F, the polymer cyclizes, that is forms a 6-member hexagon ring similar to that found in graphite. Heating in an oxygen-containing atmosphere allows oxygen to diffuse into the structure of the fiber which forms cross-links or chemical bonds between the polymer chains. The fiber is then subjected to firing and graphitization at a temperature above 2000° C up to about 3000° C in an inert atmosphere. Typical graphite fibers have tensile strengths exceeding about 150 psi $\times$ 10$^3$, a tensile modulus of about 25–30 psi $\times$ 10$^6$ and a density of about 2.

Organic precursors are generally resinous fibers such as acrylic polymers, polyvinyl alcohol, regenerated cellulose, pitch materials including petroleum resideus, asphalt and coal tars. Highly oriented, synthetic polymer precursors such as acrylic polymers and regenerated cellulose provide higher modulus products. However, such ultimate high strength properties are not necessary in the invention. Lower modulus products having the desired inert clinical behavior and excellent compatability function satisfactorily in the bone cement composition of the invention.

The form of the graphite fiber is important for proper functioning of the bone cement adhesive of the invention. Very fine filaments having a diameter below about 50 microns, typically 5 to 30 microns are very feathery. If the filaments adhere to each other, the material is feathery, difficult to handle, difficult to uniformly disperse throughout the composition and does not provide cured materials having the desired physical properties. Furthermore, the average length of the fibers should be between about 0.1 to 15 mm, preferably from about 4 to 10 mm in average length. When the average length is less than about 0.1 mm the reinforcing effect is not sufficient and when the length is more than 15 mm the viscosity of the composition in the cement stage is too low to be easily workable, and the long fibers tend to protrude from the surface causing poorer adhesion at the interfaces and creating potential sides for irritation, inflamation and unwanted tissue growth. In addition, the fibers tend to become preferentially oriented thereby destroying the isotropy of the composite material. The fibers as received from the manufacturer are usually continuous monofilaments which are chopped or cut into desired length such as 6 mm length fibers from Celanese GY-70 graphite material (individual, non-adhering filaments, 8 micron diameter).

The polymer constituent of the composition can be any methylmethacrylate polymer such as methylmethacrylate homopolymers and copolymers of methylmethacrylate with alphaethylenically unsaturated compounds such as vinyl acetate, alkyl acrylates, alkyl methacrylates and multi-functional acrylic monomers such as alkylene dimethacrylate and alkylene diacrylates and triacrylates. These polymers generally have a molecular weight between 500,000 and 2,000,000.

Pure liquid methylmethacrylate has a very high solvating action at room temperature for most organic polymers. The polymer in monomer composition can be derived from a polymerization process containing excess methylmethacrylate monomer and may contain residual free radical agents such as 0.1–0.5% by weight of benzoyl peroxide and may also include a cross-linking agent such as 1 to 5% of ethylene dimethacrylate.

The polymer in monomer syrup may be prepared by the methods described in U.S. Pat. No. 3,154,600 by heating a small amount of polymerization initiator in solution in the methacrylic ester and in the presence of a chain transfer agent having the suitable pressure and temperature. Heating is continued until the solution reaches a predetermined viscosity. Thereafter the hot solution is quenched by the addition of cold monomer containing a polymerization inhibitor.

Curing of the bone cement composition of the invention can be accomplished by any suitable initiator system such as from about 0.1 to about 3% by weight, preferably about 0.6% of a conventional free radical initiator. The initiator can be a peroxy compound of an azo compound. For purposes of biocompatability benzoyl peroxide is a very suitable free radical initiator. The curing temperature can be reduced to room temperature, e.g., about 25° to 30° C by inclusion in the formulation of an activator for the peroxide catalyst which causes more rapid decomposition of the peroxide to form free radicals. Suitable peroxide catalysts are benzoyl peroxide, 2,4-dichlorobenzoyl peroxide and 4-chlorobenzoyl peroxide. Activators or accelerators for these catalysts are N,N-dialkyl anilines or N,N-dialkyl toluidines generally employed in amounts ranging from about 0.1 to 1% based on the weight of monomer present. A preferred activator is N,N-di(2-hydroxyethyl)-p-toluidine. In order to provide longer shelf life for the compositions of the invention, the composition may be stored in a closed container at cold temperature. Bone cements containing both activator and peroxide should be made as two-part compositions in which the activator and monomer and peroxide and polymer component are packaged in separate containers.

The suitability of the graphite fiber reinforced surgical bone cement was investigated in the following experiments. The bone cement compositions were based on polymethacrylate (PPM) polymer dissolved in methylmethacrylate (MMA) monomer in which was dispersed celanese GY-70 fibers cut into approximately 6 millimeter length.

The polymer was dissolved in liquid monomer and grpahite fibers were then added to form a slurry. After considerable experimentation with fiber types, processing variables and an amount of each additive the selection of the fiber diameter length and ratio of monomer to polymer as discussed above was determined. It was found that a mixture of approximately 30% monomer, 60% polymer and 10% by weight graphite fiber gave the best results. This ratio of polymer to monomer was used in the following experiments with the ratio of graphite fibers being 10% by weight unless otherwise indicated.

Both fiber reinforced and unreinforced beam and cylinder specimens were fabricated and tested. The unreinforced specimens were geometrically similar to their fiber reinforced counterparts and were tested to provide baseline data. Several batches of each type of specimen were used in the investigation.

The unreinforced beam specimens were made by casting the mixed PMM between parallel aluminum plates shimmed to a thickness of approximately 3 mm. Individual specimens were machined to the approximate dimensions 25 × 100 mm, then measured to the nearest 0.01 mm. The specimens were tested as simply supported beams in three point bending in accordance with ASTM Specification D790.

The unreinforced cylinder specimens were made by mixing and casting the bone cement in 18 mm diameter glass tubing approximately 200 mm long. Specimens were machined to the approximate dimensions, 13 mm diameter by 25 mm long, then measured to the nearest 0.01 mm. The specimens were tested as compression samples in accordance with ASTM Specification D695.

Flexural fiber reinforced specimens were prepared by pressing the material to the required thickness with considerable force. The specimens were band sawed from the cured material which had several surface irregularities.

Compression fiber reinforced specimens were made by compressing the material into glass tubes using tightly fitting rams. Use of more loosely fitting rams was unsuccessful because liquid was squeezed out of the mix. The resulting specimens were porous and lacks uniformity of batch control.

Static tests were run to determine flexural and compressive mechanical material properties on the beam and cylinder specimens, respectively. All specimens were tested in an Instron machine at a loading rate of 1.3 mm/minute.

Average test data for the unreinforced baseline specimens are given in Table I.

TABLE I

| BATCH NO. | NO. OF SPECIMENS | DATE TYPE | AVERAGE UNTIMATE STRENGTH ($N/m^2 \times 10^{-6}$) | AVG. MODULUS OF ELASTICITY ($N/m^2 \times 10^{-6}$) |
|---|---|---|---|---|
| 1 | 6 | Compression | 85 | — |
| 2 | 3 | Compression | 82 | — |
| 3 | 3 | Compression | 84 | — |
| 4 | 3 | Flexure | 52 | 2300 |
| 5 | 3 | Flexure | 49 | 2100 |

TABLE I-continued

| BATCH NO. | NO. OF SPECIMENS | DATA TYPE | AVERAGE UNTIMATE STRENGTH ($N/m^2 \times 10^{-6}$) | AVG. MODULUS OF ELASTICITY ($N/m^2 \times 10^{-6}$) |
|---|---|---|---|---|
| 6 | 3 | Flexure | 48 | 2100 |

As can be seen from these data, the specimens were well behaved and gave repeatable results. The data for graphite reinforced specimens is presented in Table II.

TABLE II

| BATCH NO. | NO. OF SPECIMENS | DATA TYPE | FILLER RATIO (% BY WEIGHT) | AVERAGE ULT. STRENGTH ($N/m^2 \times 10^{-6}$) | AVERAGE MODULUS OF ELASTICITY ($N/m^2 \times 10^{-6}$) |
|---|---|---|---|---|---|
| 8 | 3 | Compression | 10 | 12 | — |
| 9 | 3 | Compression | 10 | 23 | — |
| 1 | 3 | Flexure | 1 | 48 | 2300 |
| 2 | 3 | Flexure | 2 | 51 | 2500 |
| 3 | 2 | Flexure | 3 | 48 | 4100 |
| 4 | 2 | Flexure | 10 | 49 | 4800 |
| 5 | 2 | Flexure | 10 | 43 | 4700 |
| 6 | 3 | Flexure | 10 | 51 | 4400 |
| 7 | 3 | Flexure | 10 | 40 | 4900 |

As indicated by the data of Table II, considerable variation and low values of compressive strength were obtained. The flexural modulus and strength values were fairly repeatable, as can be seen from the data of batches 4 through 7. Batches 1, 2 and 3 were run to test the effect of variations in fiber content on specimen response.

The exothermic temperature-time profiles of the baseline and fiber reinforced materials are shown in FIG. 1. The data were collected by means of a thermocouple embedded in a sample of each material approximately 13 mm thick by 38 mm in diameter contained in a plastic dish.

A summary of the overall average experimental results obtained from Tables I, II and FIG. 1 is given in Table III.

TABLE III

| PARAMETER | UNREINFORCED | REINFORCED |
|---|---|---|
| Flexural strength ($N/m^2 \times 10^{-6}$) | 50 | 47 |
| Compressive strength ($N/m^2 \times 10^{-6}$) | 84 | 17 |
| Modulus of Elasticity ($N/m^2 \times 10^{-6}$) | 2200 | 4600 |
| Max. Temperature exotherm (° C) | 104 | 52 |

As can be seen from the data summarized in Table III, graphite fiber additives and particularly at 10% level resulted in a significant increase in stiffness (modulus of elasticity) without compromising the flexural strength of the material. The compressive strength decreased significantly, however, as a result of poor specimen quality and the presence of voids. The exotherm also decreased significantly which is due primarily to the removal of reactants from the filled material and the inhibiting effect of the graphite fibers on the rate of reaction.

On the basis of this data, it appears that use of graphite fiber additives improves certain of the mechanical and thermal properties of surgical bone cement.

It is to be realized that only preferred embodiments of the invention have been disclosed and that numerous substitutions, alterations and modifications are all permissible without departing from the spirit and scope of the invention as defined in the following claims.

What is claimed is:

1. A method of adhering bone to the surface of a rigid substrate comprising the steps of:
    applying to the bone and surface a surgical bone cement composition comprising a dispersion of 2 to 12% by weight of high modulus graphite fibers having a diameter from 1 to 50 microns and a length from 0.1 mm to 15 mm within a biocompatible polymer dissolved in a biocompatible reactive monomer; and
    curing the cement to form an adherent flexural bond.

2. A method according to claim 1 in which the fibers are monofilamentary and non-adhering.

3. A method according to claim 1 in which the monomer is an acrylic monomer, present from 20 to 40% by weight and the polymer is an acrylic polymer soluble in the monomer and is present in an amount from 50 to 70% by weight.

4. A method according to claim 3 in which the monomer is methylmethacrylate and the polymer is polymethylmethacrylate.

5. A method according to claim 4 in which 10% by weight of the graphite fibers are present, 30% by weight of monomer are present and 60% by weight of polymer are present in the composition.

6. A method according to claim 3 in which the composition further includes from 0.1 to 3% of a biocompatible free radical catalyst and 0 to 1% by weight of an activator for the catalyst.

7. A method according to claim 1 in which the rigid substrate is a prosthetic device and the bone is living animal bone.

* * * * *